United States Patent [19]

Ribier et al.

[11] Patent Number: 5,753,241
[45] Date of Patent: May 19, 1998

[54] TRANSPARENT NANOEMULSION LESS THAN 100 NM BASED ON FLUID NON-IONIC AMPHIPHILIC LIPIDS AND USE IN COSMETIC OR IN DERMOPHARMACEUTICALS

[75] Inventors: Alain Ribier, deceased, late of Paris, by Roger Ribier, legal representative; Jean-Thierry Simonnet, Paris; Sylvie Legret, Chatillon, all of France

[73] Assignee: L'Oreal, Paris, France

[21] Appl. No.: 607,353

[22] Filed: Feb. 26, 1996

[30] Foreign Application Priority Data

Feb. 27, 1995 [FR] France ................... 95 02268

[51] Int. Cl.$^6$ .................. A61K 6/00; A61K 31/74; A01N 37/02
[52] U.S. Cl. .................. 424/401; 424/78.03; 424/195.1; 424/450; 424/525; 514/552; 514/873; 514/938; 252/304; 252/312; 252/314
[58] Field of Search .................. 424/195.1, 520–525, 424/401, 450, 78.03; 514/552, 937, 938, 873; 252/304, 312, 314

[56] References Cited

FOREIGN PATENT DOCUMENTS

| 0 334 777 A1 | 9/1989 | European Pat. Off. |
| 0 490 053 A1 | 6/1992 | European Pat. Off. |
| 0 516 508 A1 | 12/1992 | European Pat. Off. |
| 0 572 080 A1 | 12/1993 | European Pat. Off. |

OTHER PUBLICATIONS

French Search Report Dated Dec. 11, 1995.

*Primary Examiner*—Sandra E. Saucier
*Attorney, Agent, or Firm*—Oblon, Spivak, McClelland, Maier & Neustadt, P.C.

[57] ABSTRACT

An oil-in-water nanoemulsion in which the oil globules have a mean size of less than 100 nm and which contains an amphiphilic lipid component containing at least one non-ionic amphiphilic lipid which is liquid at an ambient temperature of less than 45° C. The nanoemulsion can be used in the fields of cosmetics and dermopharmaceuticals. The nanoemulsion is stable on storage, can contain significant amounts of oil while retaining good transparency, and can contain heat-sensitive active agents.

24 Claims, No Drawings

TRANSPARENT NANOEMULSION LESS THAN 100 NM BASED ON FLUID NON-IONIC AMPHIPHILIC LIPIDS AND USE IN COSMETIC OR IN DERMOPHARMACEUTICALS

SUMMARY OF THE INVENTION

The present invention relates to an oil-in-water nanoemulsion which is preferably transparent and in which the oil globules have a mean size of less than 100 nm. The invention nanoemulsion further preferably comprises an amphiphilic lipid component based on at least one non-ionic amphiphilic lipid which is liquid at temperatures less than 45° C. The invention nanoemulsion is useful for the topical application of, in particular, cosmetics, skin conditioners, and dermopharmaceuticals.

BACKGROUND OF THE INVENTION

Oil-in-water emulsions are well-known in the field of cosmetics, dermopharmaceuticals, etc., in particular for the preparation of cosmetic products such as lotions, tonics, serums or toilet waters. Transparent microemulsions are also known. Microemulsions are not, strictly speaking, emulsions; these are transparent solutions of micelles, that is to say that the oil present is dissolved therein by virtue of the joint presence of surfactants and of cosurfactants and by virtue, generally, of a high proportion of these surfactants and cosurfactants. The extremely small size of the particles, which is the cause of their transparency, arises from this "solubilization". The disadvantages of these microemulsions, however, are related to their high proportion of surfactants, leading to intolerances and resulting in a sticky feel during application to the skin. Thus, EP-A-572,080 describes microemulsions containing an oil, a fragrance and a mixture of surfactant and of cosurfactant, the proportion of oil and of mixture of surfactant and cosurfactant being between 0.85 and 2.5.

Nanoemulsions comprising oil globules having a mean size of less than 100 nm have already been used in order to obtain transparent compositions having an appearance similar to water and resulting, after application to the skin, in a feel similar to that of a cream or milk. These nanoemulsions, in contrast to microemulsions, are true emulsions where the oil globules are dispersed in an aqueous phase, the surfactants being situated at the oil/aqueous phase interface. The transparency of these emulsions arises from the small size of the oily globules, which small size is obtained by virtue of passing through a high-pressure homogenizer.

Nanoemulsions comprising an amphiphilic lipid phase composed of phosphoglycerides, water and oil are known. These emulsions have the disadvantage of being unstable on storage at conventional storage temperatures, namely between 0° and 45° C. They result in yellow compositions and produce a rancid smell which develops after a few days of storage. They are described in EP 406 162.

Nanoemulsions comprising the combination of a long-chain fatty alcohol and/or of a long-chain fatty acid and of a soap type surfactant of a long-chain fatty acid forming a gel, the phase transition temperature of which is greater than 60° C., are also known. These emulsions are prepared at temperatures greater than 70° C. which limit the use of heat-sensitive active principles in such compositions. They are described, for example, in EP-A-615,741.

The inventors have unexpectedly discovered new nanoemulsions exhibiting all the advantages of known nanoemulsions without their disadvantages nor the disadvantages of microemulsions. The invention nanoemulsions have oil globules whose mean size is less than 100 nm, and they are stable on storage between 0° and 45° C. for at least two months. The nanoemulsions in accordance with the invention are preferably prepared at temperatures between 20° and 450° C. and are compatible with heat-sensitive active principles. They can contain significant amounts of oil, while retaining good transparency properties. They can particularly contain significant amounts of fragrance and can improve their persistence. They also promote penetration of the active principles into the surface layers of the skin.

DETAILED DESCRIPTION OF THE INVENTION

The subject of the present invention is an oil-in-water nanoemulsion having oil globules, the mean size of which is less than 100 nm, and comprising an amphiphilic lipid component, characterized in that the amphiphilic lipid component comprises at least one non-ionic amphiphilic lipid which is liquid at a temperature of less than 45° C. and that the ratio by weight of the amount of oil to the amount of amphiphilic lipid component varies from 2 to 10. The invention nanoemulsions are water-containing nanoemulsions.

The amphiphilic non-ionic lipids of the invention are preferably chosen from esters or mixtures of esters of at least one polyol, preferably chosen from polyethylene glycol containing from 1 to 60 ethylene oxide units, sorbitan, glycerol containing from 2 to 30 ethylene oxide units or polyglycerols containing from 2 to 15 glycerol units, with at least one fatty acid containing at least one saturated or unsaturated, linear or branched, $C_8$–$C_{22}$ alkyl chain.

Mention may be made, by way of example, of

- the isostearate of polyethylene glycol with a molecular weight of 400, sold under the name PEG 400 isostearate by the company Unichema;
- diglyceryl isostearate, sold by the company Solvay;
- glyceryl laurate containing 2 glycerol units, sold by the company Solvay;
- sorbitan oleate, sold under the name Span 80 by the company ICI;
- sorbitan isostearate, sold under the name Nikkol SI 10R by the company Nikko;
- α-butylglucoside cocoate or α-butylglucoside caprate, marketed by the company ULICE.

The ratio by weight of the amount of oil contained in the emulsion in accordance with the invention to the amount of amphiphilic lipid component (oil/lipid) preferably varies from 3 to 6, but may be as high as 10 and includes 2, 3, 4, 5, 6, 7, 8, and 9 and all values and subranges therebetween.

A specific form of the nanoemulsion in accordance with the invention is characterized in that the amphiphilic lipid component additionally contain one or a number of ionic amphiphilic lipids.

Ionic amphiphilic lipids which may be used in the nanoemulsions of the invention include, and are preferably chosen from the group formed by neutralized anionic lipids, amphoteric ionic lipids or alkylsulphonic derivatives.

They are more preferably chosen from the group formed by:

- alkaline salts of dicetyl and dimyristyl phosphate;
- alkaline salts of cholesterol sulphate;
- alkaline salts of cholesterol phosphate;
- amino acids containing fatty groups, such as mono- and disodium acylglutamates;

sodium salts of phosphatidic acid;
phospholipids;
alkylsulphonic derivatives of formula:

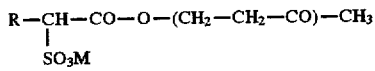

in which R represents a $C_{16}$–$C_{22}$ alkyl radical, in particular $C_{16}H_{33}$ and $C_{18}H_{37}$ radicals, taken as a mixture or separately, and M is an alkali metal, such as sodium.

The ionic amphiphilic lipids are present in the nanoemulsions of the invention in concentrations preferably ranging from 2 to 10% by weight and more preferably from 5 to 10% by weight with respect to the total weight of the amphiphilic lipid component.

The nanoemulsions in accordance with the invention contain an amount of oil preferably ranging from 5 to 30% by weight with respect to the total weight of the emulsion.

Oils which can be used in the emulsions of the invention include, and are preferentially chosen from, the group formed by:

- animal or vegetable oils formed by esters of fatty acids and of polyols, in particular liquid triglycerides, for example sunflower, maize, soybean, gourd, grape seed, sesame and hazelnut oils, fish oils or caprylic/capric triglyceride, or vegetable or animal oils of formula $R_9COOR_{10}$, in which $R_9$ represents the residue of a higher fatty acid containing from 7 to 19 carbon atoms and $R_{10}$ represents a branched hydrocarbon chain containing from 3 to 20 carbon atoms, for example purcellin oil;
- natural or synthetic essential oils such as, for example, oils of eucalyptus, of lavandin, of lavender, of vetiver, of Litsea cubeba, of lemon, of santal, of rosemary, of camomile, of savory, of nutmeg, of cinnamon, of hyssop, of caraway, of orange, of geranium, of cade and of bergamot;
- hydrocarbons, such as hexadecane and liquid paraffin;
- halogenated hydrocarbons, in particular fluorocarbons, such as fluoroamines, for example perfluorotributylamine, fluorinated hydrocarbons, for example perfluorodecahydronaphthalene, fluoroesters and fluoroethers;
- esters of an inorganic acid and of an alcohol;
- ethers and polyethers;
- silicones, as a mixture with at least one of the oils defined above, for example decamethylcyclopentasiloxane or dodecamethylcyclohexasiloxane.

The emulsions in accordance with the present invention can contain additives, in order to improve the transparency of the formulation. These additives are preferably chosen from the group formed by:

- lower $C_1$–$C_8$ alcohols, such as ethanol,
- glycols, such as glycerol, propylene glycol, 1,3-butylene glycol, dipropylene glycol or polyethylene glycols containing from 4 to 16 ethylene oxide units and preferably from 8 to 12.

Additives, such as those mentioned above, are present in the emulsions of the invention in concentrations preferably ranging from 5 to 30% by weight with respect to the total weight of the emulsion. The alcohols are preferably used at concentrations ranging from 5 to 20% by weight. The glycols are preferably used as concentrations ranging from 2 to 15% by weight.

In addition, the use of the alcohols as defined above, at concentrations greater than or equal to 15% by weight, make it possible to obtain preservative-free emulsions.

The emulsions of the invention can contain water-soluble or liposoluble active principles (agents) having a cosmetic, dermopharmaceutical, etc. activity. The liposoluble active principles are generally thought to be confined in the oily globules of the emulsion, whereas the water-soluble active principles are thought to be confined in the aqueous phase of the emulsion. Mention may be made, as examples of active principles, of vitamins, such as vitamin E and its derivatives, provitamins, such as panthenol, humectants, sunscreens, etc.

The nanoemulsions in accordance with the invention can also contain adjuvants used for the formulation of the nanoemulsion in the form of a lotion, serum, cream or milk, such as gelling agents, preservatives and fragrances. Mention may be made, among the gelling agents which can be used, of cellulose derivatives, such as hydroxypropyl methyl cellulose, fatty alcohols such as stearyl, cetyl and behenyl alcohols, alga derivatives such as satiagum, natural gums such as gum tragacanth and synthetic polymers such as the mixtures of polycarboxyvinyl acids marketed under the name Carbopol by the company Goodrich and the mixture of Na acrylate/acrylamide copolymers marketed under the name Hostacerin PN 73 by the company Hoechst.

The oil globules of the nanoemulsions of the invention preferably have a mean size ranging from 30 to 75 nm and more preferentially from 40 to 60 nm. They can be as large as less than 100 nm and include 5, 10, 15, 20, 25, 30, 35, 40, 45, 50, 55, 60, 65, 70, 75, 80, 85, 90, and 95 nm and all values and subranges therebetween. The size of the globules makes it possible to promote penetration of the active principles into the surface layers of the skin (carrier effect).

The nanoemulsions according to the invention are preferably colorless or possibly slightly bluish and exhibit a transparency, determined by the transmittance coefficient, measured at a wavelength of 600 nm, preferentially ranging from 30 to 90% and more particularly from 50 to 80%.

The nanoemulsions of the invention can be obtained by a process, characterized in that the aqueous phase and the oily phase are mixed, with vigorous stirring, at an ambient temperature of less than 45° C. followed by high-pressure homogenization at a pressure greater than $10^8$ Pa and preferably ranging from $12 \times 10^7$ to $18 \times 10^7$ Pa. Such a process makes it possible to produce, at ambient temperature, nanoemulsions which are compatible with heat-sensitive active compounds and which can contain significant amounts of oils and in particular fragrances which contain fatty substances, without denaturing them.

Further subjects of the invention are a composition for topical use such as a cosmetic or dermopharmaceutical composition, characterized in that it is composed of an emulsion as defined above, and the use of the same on the skin, hair, eyes, face, etc.

A further subject of the invention is the use of the nanoemulsions as defined above as the basis for care and/or make-up products for the skin and/or the face and/or the scalp, such as lotions, serums, milks, creams or toilet waters.

Finally, the invention also relates to a non-therapeutic process for caring for the skin or for the scalp, characterized in that a nanoemulsion as defined above is applied to the skin or to the scalp.

The following examples will make it possible to understand the invention better without, however, having a limiting nature.

EXAMPLES

For the following Examples 1 to 7, the following procedure is used:

- the amphiphilic lipids are homogenized with the oils and the lipophilic active principles and adjuvants at a temperature of 45° C. in a first phase A;

the hydrophilic active principles and adjuvants are dissolved at a temperature of 20° to 30° C. in a second phase B;

then, the phases A and B are mixed using a turbine homogenizer and then homogenization is carried out using a high-pressure homogenizer of the Soavi-Niro type at a pressure of 1500 bars, over 7 passages, the temperature of the product being maintained below 35° C.

In the case of Example 7, the gelling agent is added in a phase C which is mixed with the phases A and B using a turbine homogenizer.

Example 1

Vitamin-Containing Care Water

First Phase

| | |
|---|---|
| PEG-400 isostearate, sold by the company Unichema | 4.5% |
| Disodium salt of N-stearoyl-L-glutamic acid, marketed under the name Acylglutamate HS21 by the Company Ajinomoto (ionic amphiphilic lipid) | 0.5% |
| Jojoba oil | 6% |
| Mixture of sunflower, hybrid sunflower, musk rose and blackcurrant seed oils | 6% |
| Cyclomethicone | 7% |
| Vitamin E acetate | 1% |
| Copherol F1300, marketed by Henkel | 0.2% |
| Stabilized vitamin A palmitate | 0.1% |
| Non-denatured absolute ethanol | 15% |

Second Phase

| | |
|---|---|
| Demineralized water | 54.7% |
| Glycerol | 5% |

An emulsion is obtained in which the size of the oil globules is 63 nm with a transparency, determined by the transmittance coefficient at 600 nm, equal to 40%.

Example 2

Care Fluid

First Phase

| | |
|---|---|
| PEG-400 isostearate, sold by the company Unichema | 4.5% |
| Disodium salt of N-stearoyl-L-glutamic acid, marketed under the name Acylglutamate HS21 by the Company Ajinomoto (ionic amphiphilic lipid) | 0.5% |
| Jojoba oil | 5% |
| Avocado oil | 5% |
| Volatile silicone | 9% |
| Cetyl alcohol | 1% |
| Vitamin E acetate | 1% |
| Copherol F1300 | 0.2% |
| Stabilized vitamin A palmitate | 0.1% |
| Non-denatured absolute ethanol | 15% |

Second Phase

| | |
|---|---|
| Glycerol | 5% |
| Demineralized water q.s. for | 100% |

A thick transparent emulsion is obtained in which the size of the globules is 53 nm and the transparency 60%.

Example 3

Fluid Eyeliner

First Phase

| | |
|---|---|
| PEG-400 isostearate, sold by the company Unichema | 4.5% |
| Disodium salt of N-stearoyl-L-glutamic acid, marketed under the name Acylglutamate HS21 by the Company Ajinomoto (ionic amphiphilic lipid) | 0.5% |
| Jojoba oil | 5% |
| Light liquid petrolatum | 4% |
| Avacado oil | 4% |
| Volatile silicone | 6% |
| Vitamin E acetate | 1% |
| Copherol F1300 | 0.2% |

Second Phase

| | |
|---|---|
| Glycerol | 5% |
| Polyethylene glycol containing 8 ethylene oxide units | 10% |
| Demineralized water q.s. for | 100% |

An opalescent emulsion is obtained in which the size of the globules is 65 nm and the transparency 42%.

Example 4

Body Care Fluid

First Phase

| | |
|---|---|
| PEG-400 isostearate, sold by the company Unichema | 4.5% |
| Disodium salt of N-stearoyl-L-glutamic acid, marketed under the name Acylglutamate HS21 by the company Ajinomoto (ionic amphiphilic lipid) | 0.5% |
| Light liquid petrolatum | 7% |
| Avocado oil | 7% |
| Volatile silicone | 6% |
| Vitamin E acetate | 1% |
| Non-denatured absolute ethanol | 15% |

Second Phase

| | |
|---|---|
| Glycerol | 5% |
| Demineralized water q.s. for | 100% |

A particularly fluid fluid is obtained in which the size of the globules is of the order of 50 nm and the transparency 60%.

Example 5

Moisturizing Fluid

First Phase

| | |
|---|---|
| α-Butylglucoside cocoate, marketed by ULICE | 4.5% |
| Disodium salt of N-stearoyl-L-glutamic acid, marketed under the name Acylglutamate HS21 by the Company Ajinomoto (ionic amphiphilic lipid) | 0.5% |
| Jojoba oil | 5% |
| Avocado oil | 5% |
| Volatile silicone | 6% |
| Stearyl heptanoate/stearyl caprylate | 2% |

-continued

| Vitamin E acetate | 1% |
| Non-denatured absolute ethanol | 15% |

Second Phase

| Glycerol | 6% |
| Sodium hyaluronate | 0.10% |
| Demineralized water q.s. for | 100% |

A transparent emulsion is obtained in which the size of the globules is 52 nm and the transparency 58%.

Example 6

Scented Fluid

First Phase

| PEG-400 isostearate, sold by the company Unichema | 4.5% |
| Disodium salt of N-stearoyl-L-glutamic acid, marketed under the name Acylglutamate HS21 by the Company Ajinomoto (ionic amphiphilic lipid) | 0.5% |
| Jojoba oil | 4% |
| Mixture of sunflower, hybrid sunflower, musk rose and blackcurrant seed oils | 4% |
| Volatile silicone | 6% |
| Fragrance | 6% |
| Non-denatured absolute ethanol | 15% |

Second Phase

| Demineralized water | 54.7% |
| Glycerol | 5% |
| Demineralized water q.s. for | 100% |

A scented lotion of high persistence is obtained in which the size of the oil globules is 50 nm with a transparency equal to 54%.

Example 7

Scented Balm

First Phase

| α-Butylglucoside cocoate, marketed by ULICE | 4.5% |
| Disodium salt of N-stearoyl-L-glutamic acid, marketed under the name Acylglutamate HS21 by the Company Ajinomoto (ionic amphiphilic lipid) | 0.5% |
| Mixture of sunflower, hybrid sunflower, musk rose and blackcurrant seed oils | 7% |
| Light liquid petrolatum | 7% |
| Volatile silicone | 6% |
| Fragrance | 1.5% |
| Vitamin E acetate | 0.5% |
| Non-denatured absolute ethanol | 15% |

Second Phase

| Glycerol | 5% |
| Sterile demineralized water q.s. for | 100% |

Third Phase

| Hydroxypropyl cellulose, marketed under the name Methocel E 4 M QG by the company Dow Chemical | 0.4% |
| Sterile demineralized water | 15% |

A smooth non-sticky balm is obtained in which the size of the globules is 54 nm and the transparency 53%.

In addition to the specific examples of various components of the invention nanoemulsions given above, those compounds and compositions meeting the functional requirements of the invention components listed in Volumes 1 and 2 of the International Cosmetic Ingredient Dictionary, 6th Ed., 1995, J. A. Wenninger, et al, Eds., published by the Cosmetic, Toiletry and Fragrance Association, incorporated herein by reference, are also to be included. Moreover, each invention component may be a mixture of acceptable compounds or compositions.

This application is based on French Patent Application 95-02268, filed Feb. 27, 1995, incorporated herein by reference.

What is claimed:

1. An oil-in-water nanoemulsion comprising water, oil globules having a mean size of less than 100 nm dispersed in an aqueous phase and an amphiphilic lipid component situated at the oil/aqueous phase interface wherein the amphiphilic lipid component comprises at least one non-ionic amphiphilic lipid which is liquid at a temperature of less than 45° C. and wherein the ratio by weight of the amount of oil to the amount of amphiphilic lipid component is from 3 to 10.

2. The nanoemulsion according to claim 1, wherein the non-ionic amphiphilic lipid is an ester or a mixture of esters of at least one polyol, selected from the group consisting of polyethylene glycol containing from 1 to 60 ethylene oxide units, sorbitan, glycerol containing from 2 to 30 ethylene oxide units and polyglycerol containing from 2 to 15 glycerol units, with at least one fatty acid containing at least one saturated or unsaturated, linear or branched, $C_8$–$C_{22}$ alkyl chain.

3. The nanoemulsion according to claim 1 wherein the ratio by weight of the amount of oil to the amount of amphiphilic lipid component is from 3 to 6.

4. The nanoemulsion according to claim 1 wherein the amphiphilic lipid component further comprises at least one ionic amphiphilic lipid.

5. The nanoemulsion according to claim 4, wherein the at least one ionic amphiphilic lipid is selected from the group consisting of neutralized anionic lipids, amphoteric ionic lipids and alkylsulphonic derivatives.

6. The nanoemulsion according to claim 4 wherein the at least one ionic amphiphilic lipid is selected from the group consisting of:

alkaline salts of dicetyl and dimyristyl phosphate;

alkaline salts of cholesterol sulphate;

alkaline salts of cholesterol phosphate;

salts of amino acids containing fatty groups;

sodium salts of phosphatidic acid;

phospholipids; and alkylsulphonic derivatives of formula:

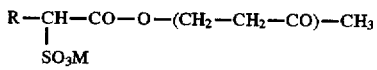

in which R represents $C_{16}-C_{22}$ alkyl radicals, taken as a mixture or separately, and M is an alkali metal.

7. The nanoemulsion according to claim 4 wherein the ionic amphiphilic lipid is present in concentrations ranging from 2 to 10% by weight with respect to the total weight of the amphiphilic lipid component.

8. The nanoemulsion according to claim 1 wherein the proportion of oil is from 5 to 30% by weight with respect to the total weight of the nanoemulsion.

9. The nanoemulsion according to claim 1 wherein the oil is selected from the group consisting of:
   animal or vegetable oils formed by esters of fatty acids and of polyols
   vegetable or animal oils of formula $R_9COOR_{10}$, in which $R_9$ represents the residue of a higher fatty acid containing from 7 to 19 carbon atoms and $R_{10}$ represents a branched hydrocarbon chain containing from 3 to 20 carbon atoms;
   natural or synthetic essential oils;
   hydrocarbons;
   halogenated hydrocarbons;
   esters of an inorganic acid and of an alcohol;
   ethers and polyethers; and
   silicones, as a mixture with at least one of the oils defined above.

10. The nanoemulsion according to claim 1 further comprising an additive that improves transparency.

11. The nanoemulsion according to claim 10, wherein the additive is a lower alcohol or glycol.

12. The nanoemulsion according to claim 11 wherein the additive is present in concentrations ranging from 5 to 30% by weight with respect to the total weight of the nanoemulsion.

13. The nanoemulsion according to claim 12, said nanoemulsion containing a lower alcohol in a concentration ranging from 5 to 20% by weight with respect to the total weight of the emulsion.

14. The nanoemulsion according to claim 12, said nanoemulsion containing a glycol in concentrations ranging from 2 to 15% by weight with respect to the total weight of the emulsion.

15. The nanoemulsion according to claim 11, said nanoemulsion comprising at least 15% by weight of said lower alcohol with respect to the total weight of the composition.

16. The nanoemulsion according to claim 1 further comprising a water-soluble or liposoluble cosmetic or dermopharmaceutical active agent.

17. The nanoemulsion according to claim 1, further comprising an additive selected from the group consisting of gelling agents, preservatives and fragrances.

18. The nanoemulsion according to claim 1 wherein the oil globules have a mean size ranging from 30 to 75 nm.

19. The nanoemulsion according to claim 1 wherein the oil globules have a mean size ranging from 40 to 60 nm.

20. The nanoemulsion according to claim 1, wherein said nanoemulsion has a transparency, determined by the transmittance coefficient, measured at a wavelength of 600 nm, ranging from 30 to 90%.

21. A composition for topical use comprising the nanoemulsion according to claim 1.

22. A process for the treatment of the skin and/or of the scalp, comprising applying a nanoemulsion according to claim 1 to the skin and/or the scalp.

23. A process for the preparation of the nanoemulsion as defined in claim 1, comprising mixing an aqueous phase and an oily phase together with stirring at a temperature of less than 45° C. to form a mixture and then carrying out high-pressure homogenization at a pressure greater than $10^8$ Pa on said mixture.

24. The process according to claim 23, wherein the pressure is from $12 \times 10^7$ to $18 \times 10^7$ Pa.

\* \* \* \* \*